(12) United States Patent
Mou et al.

(10) Patent No.: US 10,775,276 B2
(45) Date of Patent: Sep. 15, 2020

(54) PORTABLE GAS DETECTING DEVICE

(71) Applicant: Microjet Technology Co., Ltd., Hsinchu (TW)

(72) Inventors: Hao-Jan Mou, Hsinchu (TW);
Shih-Chang Chen, Hsinchu (TW);
Chiu-Lin Lee, Hsinchu (TW);
Ching-Sung Lin, Hsinchu (TW);
Chi-Feng Huang, Hsinchu (TW);
Yung-Lung Han, Hsinchu (TW);
Chun-Yi Kuo, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 16/406,634

(22) Filed: May 8, 2019

(65) Prior Publication Data
US 2019/0376877 A1 Dec. 12, 2019

(30) Foreign Application Priority Data
Jun. 8, 2018 (TW) .............................. 107119929 A

(51) Int. Cl.
| | |
|---|---|
| *G01N 1/14* | (2006.01) |
| *G01N 33/00* | (2006.01) |
| *F04B 43/04* | (2006.01) |

(52) U.S. Cl.
CPC ............ *G01N 1/14* (2013.01); *F04B 43/046* (2013.01); *G01N 33/004* (2013.01); *G01N 33/0073* (2013.01); *B81B 2201/036* (2013.01)

(58) Field of Classification Search
CPC ... B81B 2201/036; F04B 43/046; G01N 1/14; G01N 1/22; G01N 33/004; G01N 33/0073
See application file for complete search history.

(56) References Cited

U.S. PATENT DOCUMENTS

2005/0229675 A1    10/2005   Haupt et al.
2018/0187669 A1*   7/2018    Liao ..................... F04B 45/047
(Continued)

FOREIGN PATENT DOCUMENTS

| CN | 103411864 A | 11/2013 |
|---|---|---|
| TW | M525446 U | 7/2016 |

OTHER PUBLICATIONS

Taiwan Office Action for application No. 107119929 dated Jan. 11, 2019.

*Primary Examiner* — Francis C Gray
(74) *Attorney, Agent, or Firm* — Birch, Stewart, Kolasch & Birch, LLP

(57) ABSTRACT

A portable gas detecting device includes at least one detecting chamber, at least one gas sensor and at least one actuator. The gas sensor is disposed in the detecting chamber and configured for monitoring gas inside the detecting chamber. The actuator is disposed in the detecting chamber and includes a piezoelectric actuator. When an actuating signal is applied to the piezoelectric actuator and the piezoelectric actuator generates a resonance effect, the gas outside the detecting chamber is introduced into the detecting chamber for sampling. The actuator is driven by an instantaneous sampling pulse to control a trace of gas to flow into the detecting chamber for forming a stable airflow environment. In the stable airflow environment, a gas molecule is dissolved in or bonded to a reaction material on a surface of the gas sensor for reacting.

11 Claims, 10 Drawing Sheets

(56) References Cited

U.S. PATENT DOCUMENTS

2019/0234839 A1\* 8/2019 Mou .................... G01N 1/2273
2019/0302075 A1\* 10/2019 Mou .................... F04B 43/046
2019/0331558 A1\* 10/2019 Mou .................... F04B 45/047
2019/0353157 A1\* 11/2019 Mou .................... F04B 43/046

\* cited by examiner

PORTABLE GAS DETECTING DEVICE

FIELD OF THE INVENTION

The present disclosure relates to a portable gas detecting device, and more particularly to a portable gas detecting device driven by an instantaneous sampling pulse for gas detection.

BACKGROUND OF THE INVENTION

Nowadays, people pay much attention to the air quality in the environment. For example, it is important to monitor carbon monoxide, carbon dioxide, volatile organic compounds (VOC), Particulate Matter 2.5 (PM2.5), nitric oxide, sulfur monoxide, and so on. The exposure of these substances in the environment will cause human health problems or even harm the life. Therefore, it is important for every country to monitor the air quality in the environment, which is a topic currently being valued.

Generally, it is feasible to use a gas sensor to monitor the air quality in the environment. If the gas sensor is capable of immediately providing people with the monitored information relating to the environment for caution, it may help people escape or prevent from the injuries and influence on human health caused by the exposure of the substances described above in the environment. In other words, the gas sensor is suitably used for monitoring the ambient air in the environment.

Currently, to achieve reaction detection, the gas is transported to the reaction material of a surface of the gas sensor, and thus gas monitoring is performed. Moreover, as shown in FIG. 1, the gas sensor 2 is usually disposed in a separated detecting chamber 1 for performing gas detection, and thus the detected gas would not be interfered by external factors. The detecting chamber 1 has an inlet 1a and an outlet 1b. The external gas enters the detecting chamber 1 through the inlet 1a by natural convection and flows slowly, after which the gas is spread to the surface of the gas sensor 2 for performing the reaction detecting, and discharged through the outlet 1b, so that the gas detection is achieved. Since the gas to be monitored by the gas sensor 2 is guided into the detecting chamber 1 by natural convection, it takes too long to transport the gas so that the sensing efficiency of the gas sensor 2 is negatively affected, and the immediate detection cannot be achieved.

In order to solve the above-mentioned problem and achieve the immediate detection, a fan (not shown) is assembled in the detecting chamber 1. Generally, a conventional fan is rotary motor-driven type. Although the fan speeds up the gas transportation to the detecting chamber 1, the sensitivity of sensing by the gas sensor 2 may be affected and distorted as the flow rate of the gas increases or chaos airflow occurs. This is because the gas molecule cannot be caught by the gas sensor 2 immediately for being dissolved in or bonded to the reaction material on the surface of the gas sensor 2. In addition, it takes time for the reaction material to react with the caught gas molecule. Therefore, a stable airflow of the gas flowing over the surface of the gas sensor 2 is required. The way of increasing the flow rate of gas by the fan is not suitable because it would cause high flow rate or chaos airflow. Moreover, as the fan is utilized to increase the flow rate of gas, a period of acceleration time is required for driving the fan while the fan is activated, so that the fan is driven to rotate at a specific rotational speed and generate high flow rate of gas. In addition, a period of deceleration time is required for stopping the fan from rotating. Therefore, when the fan is activated or deactivated, a period of acceleration time or deceleration time is required as the fan is driven in an inertial way. Since activating and deactivating the fan both take a period of time, adopting the fan to increase the flow rate of gas is not suitable for immediate detection. Consequently, there is a need of making the gas transportation appropriate for achieving the immediate detection.

There is a need to improve the gas sensor in monitoring the gas with accurate sensitivity and immediate response. In addition, there is a need of miniaturizing the gas sensor and the detecting chamber for possessing portability and monitoring everywhere and any time. If the fan is utilized to increase the flow rate of gas, the volume of the fan is hard to be miniaturized. Consequently, the present disclosure provides a portable gas detecting device capable of monitoring and sampling immediately.

SUMMARY OF THE INVENTION

An object of the present disclosure provides a portable gas detecting device including at least one detecting chamber, at least one gas sensor and at least one actuator. The actuator is actuated to drive the flow of gas and improve the efficiency of monitoring. The actuator is driven by a pulse to start sampling in the detecting chamber immediately. A trace of gas is controlled to flow into the detecting chamber to form a stable airflow environment. In the stable airflow environment, the gas molecule is dissolved in or bonded to the reaction material on the surface of the gas sensor for reacting. Therefore, the gas sensor possesses accurate sensitivity and monitors with immediate response. In addition, a partition is disposed in the detecting chamber for separating the gas sensor and the actuator from each other. Meanwhile, the gas sensor and the actuator are prevented from interfering each other. Moreover, the structure of the actuator is miniaturized, which benefits miniaturization of the whole device to which the actuator is applied. Therefore, the device is portable and is allowed to monitor everywhere and any time.

In accordance with an aspect of the present disclosure, a portable gas detecting device is provided. The portable gas detecting device includes at least one detecting chamber, at least one gas sensor and at least one actuator. The at least one detecting chamber has at least one inlet and at least one outlet. The at least one gas sensor is disposed in the detecting chamber and is configured for monitoring gas inside the detecting chamber. The at least one actuator is disposed in the detecting chamber. The at least one actuator includes a piezoelectric actuator. When an actuating signal is applied to the piezoelectric actuator and the piezoelectric actuator generates a resonance effect, the gas outside the detecting chamber is introduced into the detecting chamber for sampling. The actuator is driven by an instantaneous sampling pulse to control a trace of gas to flow into the detecting chamber for forming a stable airflow environment. In the stable airflow environment, a gas molecule of the gas is dissolved in or bonded to a reaction material on a surface of the gas sensor for reacting, so that the gas sensor monitors the gas with immediate response to maintain sensitivity of monitoring.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
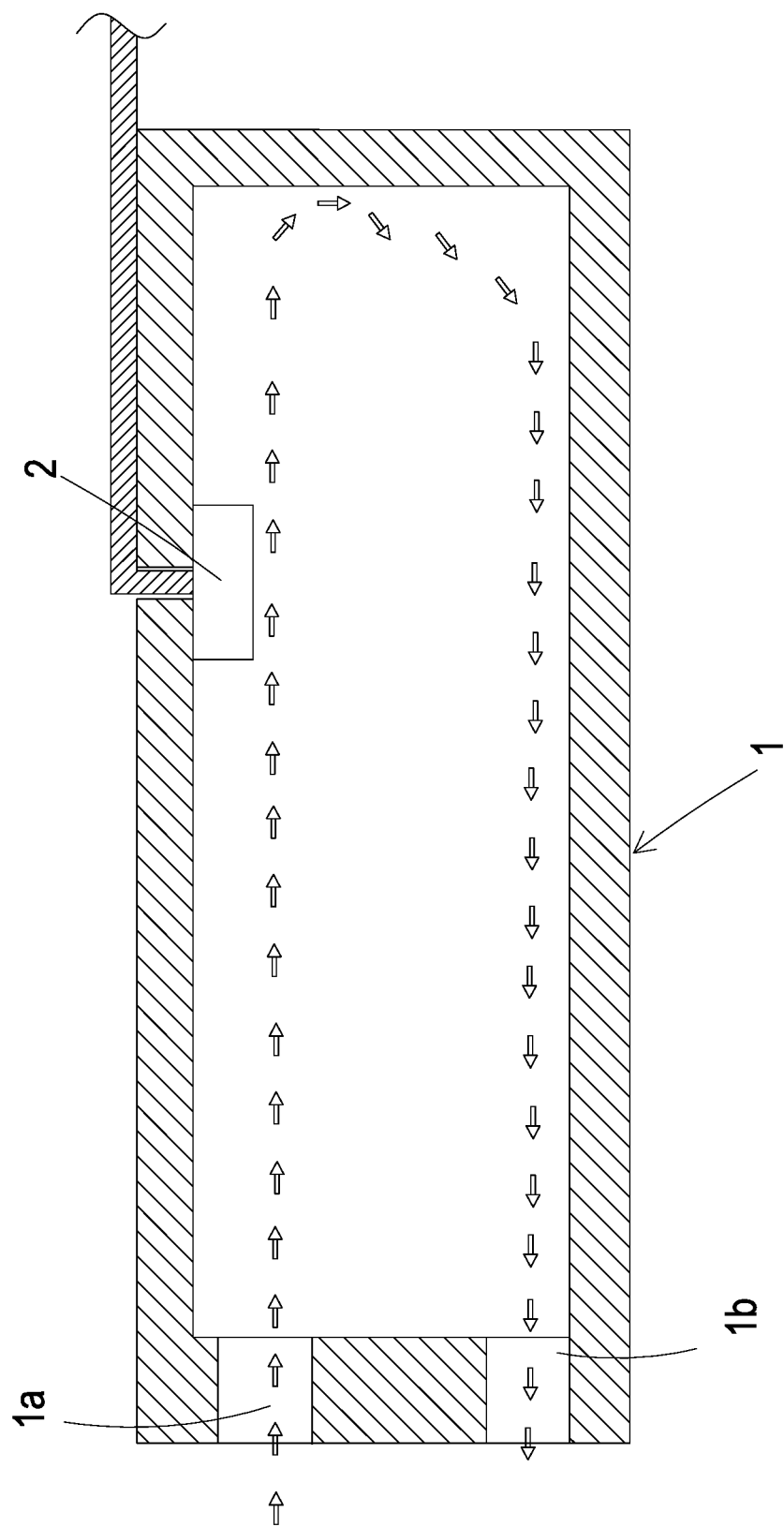
FIG. 1 is a schematic cross-sectional view illustrating a detecting chamber of a conventional gas detecting device.
Figure 2:
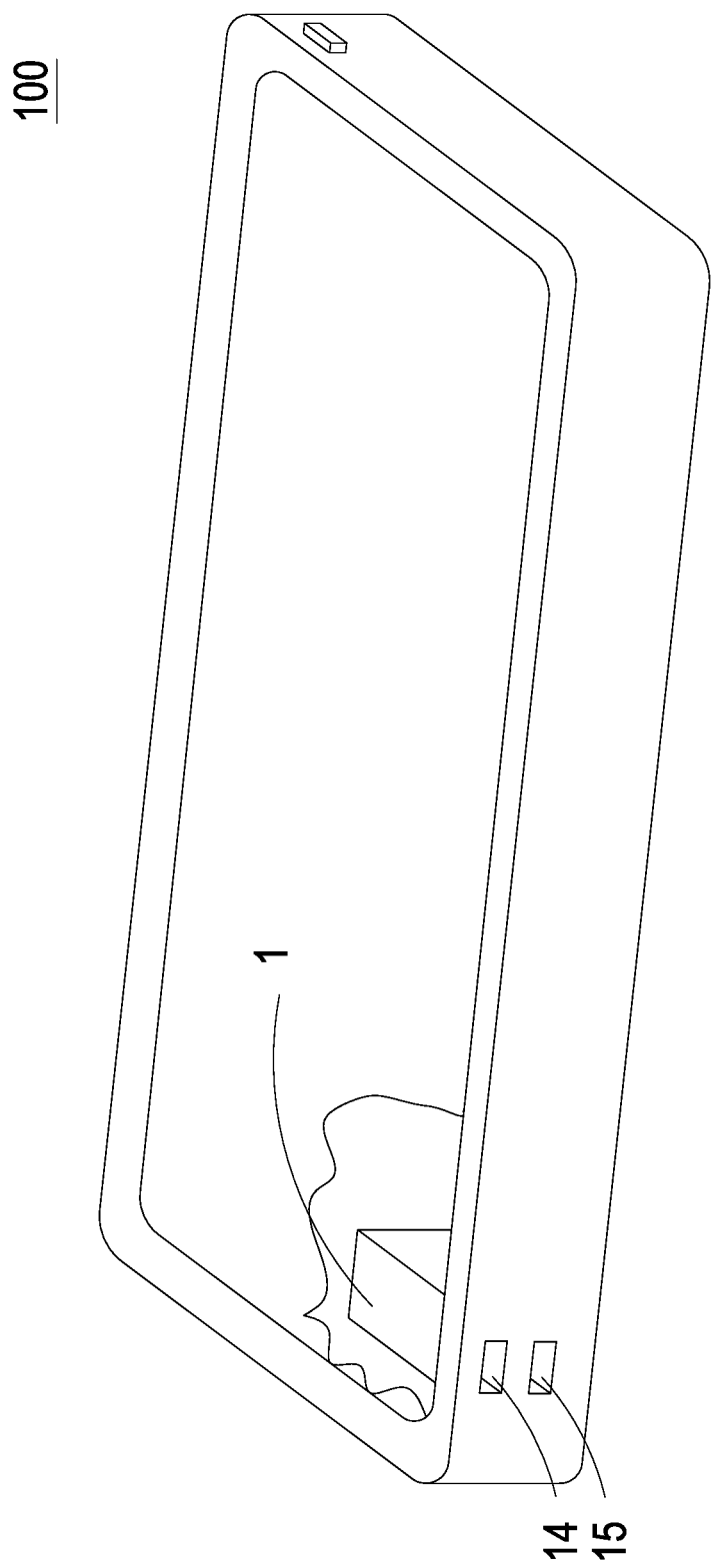
FIG. 2 is a schematic perspective view illustrating a portable gas detecting device according to an embodiment of the present disclosure.
Figure 3:
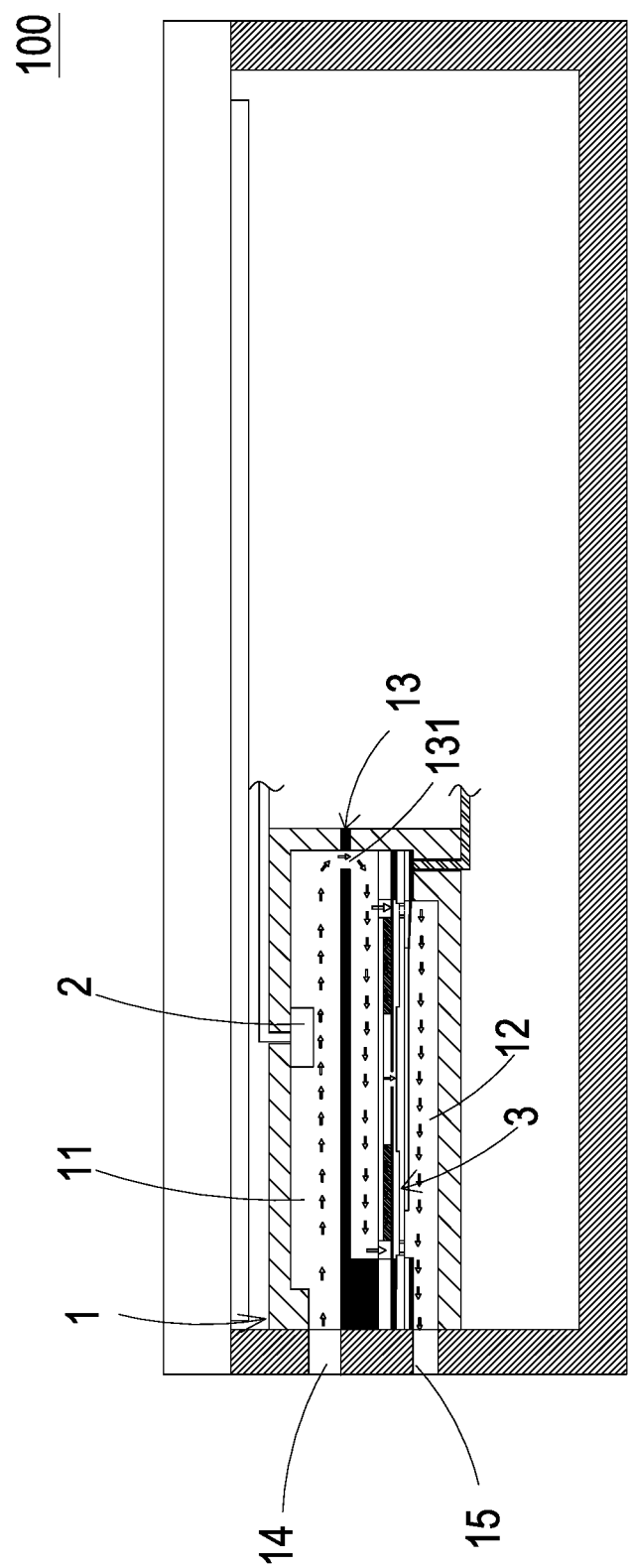
FIG. 3 is a schematic cross-sectional view illustrating a detecting chamber of the portable gas detecting device of the present disclosure.
Figure 4A:
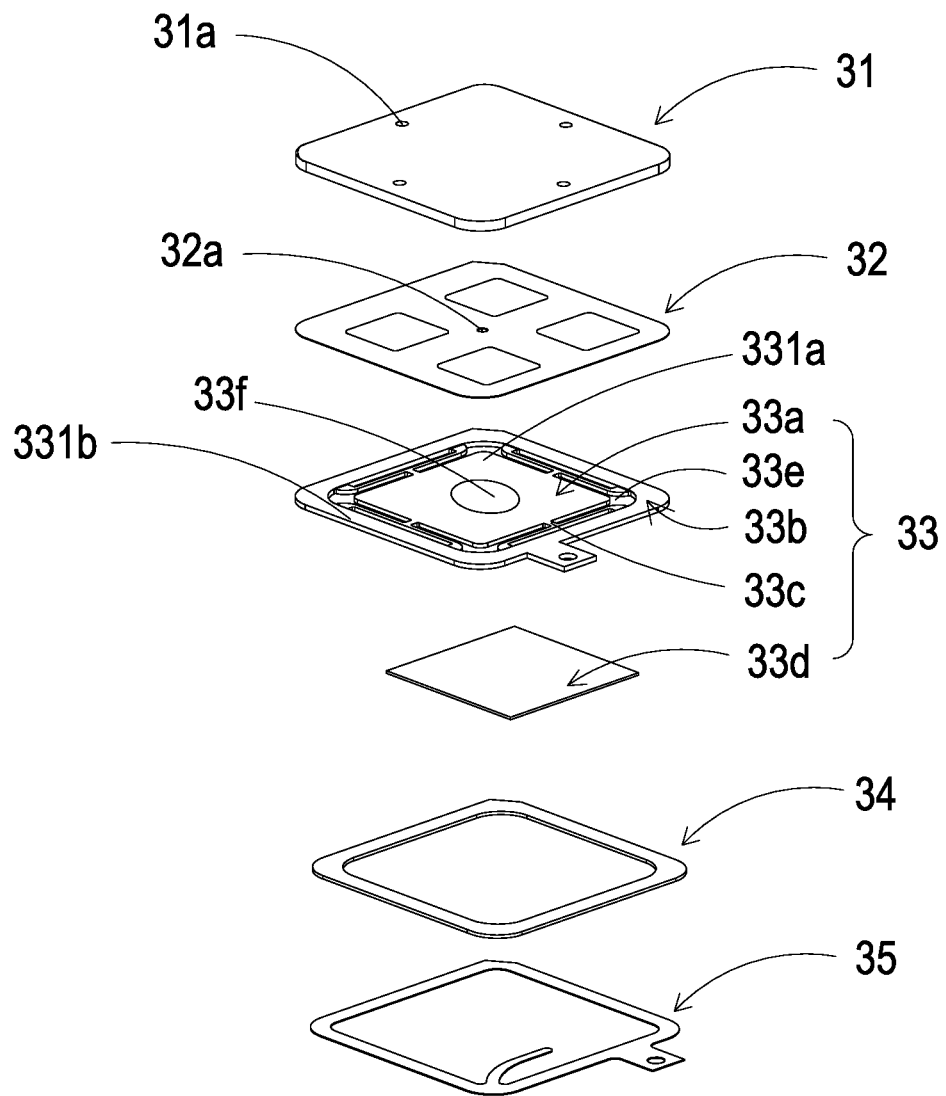
FIG. 4A is a schematic exploded view illustrating an actuator of the portable gas detecting device of the present disclosure.
Figure 4B:
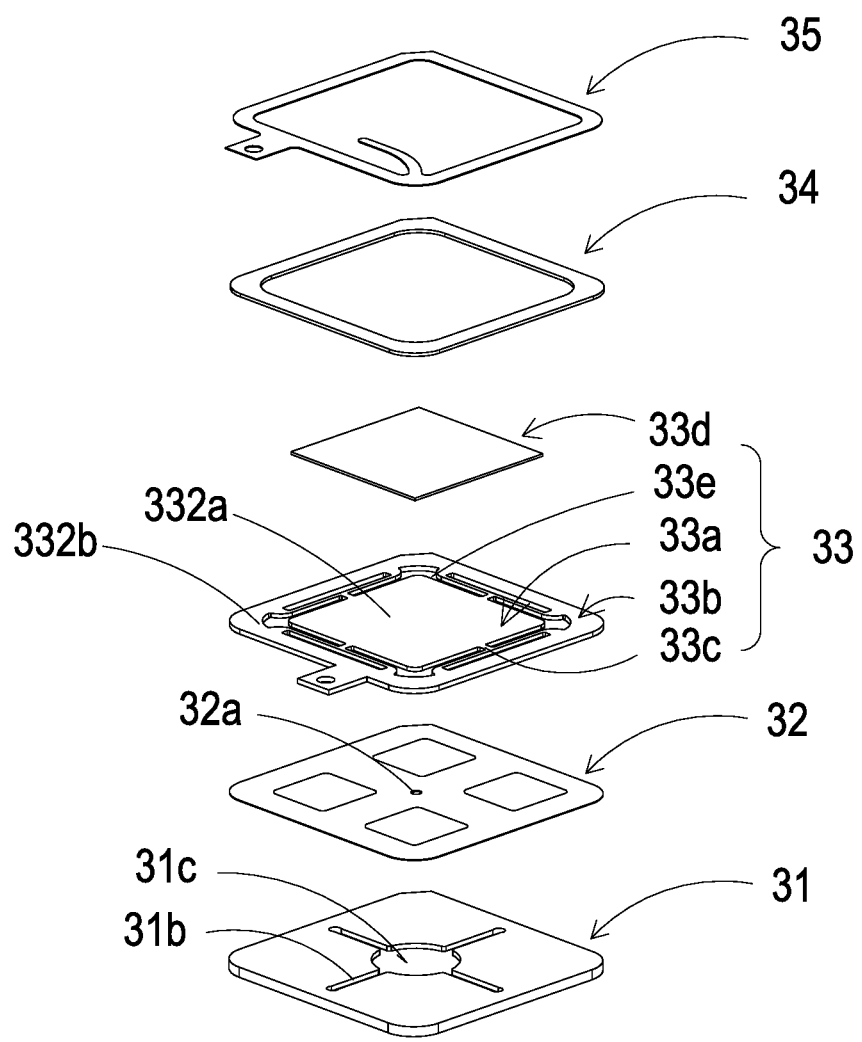
FIG. 4B is a schematic exploded view illustrating the actuator of the portable gas detecting device of the present disclosure from another viewpoint.

Please refer to FIG. 2 and FIG. 3. The present disclosure provides a portable gas detecting device 100 including at least one detecting chamber 1, at least one gas sensor 2 and at least one actuator 3. In the embodiment shown in FIG. 3, the detecting chamber 1, the gas sensor 2 and the actuator 3 are exemplified by one for each but not limited thereto. In this embodiment, the detecting chamber 1 is disposed in the portable gas detecting device 100 to form an independent separated chamber. An interior space inside the detecting chamber 1 is divided into a first compartment 11 and a second compartment 12 by a partition 13. The detecting chamber 1 has at least one inlet 14 and at least one outlet 15, but not limited thereto. The inlet 14 is in fluid communication with the first compartment 11, and the outlet 15 is in fluid communication with the second compartment 12. The partition 13 has a communicating hole 131, and the first compartment 11 and the second compartment 12 are in fluid communication with each other through the communicating hole 131. Therefore, a gas channel (the path indicated by the arrows shown in FIG. 3) for one-way gas transportation is formed inside the detecting chamber 1 by the inlet 14, the first compartment 11, the communicating hole 131, the second compartment 12 and the outlet 15. The gas sensor 2 is disposed in the first compartment 11, so that the gas outside the detecting chamber 1 can flow over the inlet 14 to a surface of the gas sensor 2 to be detected. The gas sensor 2 may be at least one selected from the group consisting of an oxygen sensor, a carbon monoxide sensor, a carbon dioxide sensor, a temperature sensor, an ozone sensor, a volatile organic compound (VOC) sensor and combinations thereof.

The actuator 3 is disposed within the second compartment 12 and sealingly divides the inner space of the second compartment 12 into two separate rooms. The actuator 3 is exemplified by one in the embodiment shown in FIG. 3 but not limited thereto. There may be a plurality of actuators 3 disposed within the second compartment 12. In this embodiment, the edges of the actuator 3 are respectively connected to the inner walls of the second compartment 12, so that the actuator 3 is fixed within the second compartment 12, and sealingly divides the inner space of the second compartment 12 into two separate rooms. The actuator 3 is actuated to transport the gas, so that a negative pressure is formed in the first compartment 11. The negative pressure allows the gas to be inhaled through the inlet 14 to the first compartment 11, the gas passes over the surface of the gas sensor 2, and the gas flows through the communicating hole 131 to the second compartment 12. As the actuator 3 is continuously actuated to transport the gas, the gas in the second compartment 12 is pushed and discharged from the outlet 15 into the environment outside the detecting chamber 1. Consequently, the one-way gas transportation is realized. The gas sensor 2 is disposed in the first compartment 11 and is separated from the actuator 3 by the partition 13. As the actuator 3 is actuated to transport the gas, the heat is generated due to the continuous vibration of the actuator 3 at high speed during operation. Under this circumstance, the partition 13 can function as a barrier, and suppress the interference caused by the generated heat. The partition 13 prevents the generated heat from interfering the sensing sensitivity of the gas sensor 2. Moreover, through disposing the detecting chamber 1 inside the portable gas detecting device 100 as an independent separated chamber, the gas sensor 2 is also isolated from the interfering factors (e.g. the interfering substances such as the heat and gas pollution generated within the portable gas detecting device 100) caused by other components of the portable gas detecting device 100. Besides, the actuator 3, which is disposed for introducing and discharging the gas, enhances the rate of transporting the gas to the surface of the gas sensor 2, so that the sensing efficiency of the gas sensor 2 is increased. The present disclosure achieves the purpose of monitoring the gas that can reflect the actual condition in the environment by the portable gas detecting device 100. In other words, the characteristic of the gas to be monitored in the portable gas detecting device 100 is the same as the characteristic of the gas outside the portable gas detecting device 100, and the interfering factors are isolated.

After the descriptions about the characteristic of the portable gas detecting device 100, the structure and actions of the actuator 3 are described as follows.

Please refer to FIGS. 4A to 5D. In an embodiment, the actuator 3 is a gas pump. The actuator 3 includes a gas inlet plate 31, a resonance plate 32, a piezoelectric actuator 33, an insulation plate 34 and a conducting plate 35, which are stacked on each other sequentially. The gas inlet plate 31 has at least one inlet aperture 31a, at least one convergence channel 31b and a convergence chamber 31c. The number of the inlet aperture 31a is the same as the number of the convergence channel 31b. In this embodiment, the number of the inlet aperture 31a and the convergence channel 31b is exemplified by four for each but not limited thereto. The four inlet apertures 31a penetrate through the four convergence channels 31b respectively, and the four convergence channels 31b converge to the convergence chamber 31c.

The resonance plate 32 is assembled on the gas inlet plate 31 by attaching. The resonance plate 32 has a central aperture 32a, a movable part 32b and a fixed part 32c. The central aperture 32a is located in the center of the resonance plate 32 and is aligned with the convergence chamber 31c of the gas inlet plate 31. The region of the resonance plate 32 around the central aperture 32a and corresponding to the convergence chamber 31c is the movable part 32b. The region of the periphery of the resonance plate 32 securely attached on the gas inlet plate 31 is the fixed part 32c.

The piezoelectric actuator 33 includes a suspension plate 33a, an outer frame 33b, at least one bracket 33c, a piezoelectric element 33d, at least one vacant space 33e and a bulge 33f. The suspension plate 33a is a square suspension plate having a first surface 331a and a second surface 332a opposite to the first surface 331a. The outer frame 33b is disposed around the periphery of the suspension plate 33a. The outer frame 33b has an assembling surface 331b and a bottom surface 332b opposite to the assembling surface 331b. The at least one bracket 33c is connected between the suspension plate 33a and the outer frame 33b for elastically supporting the suspension plate 33a. The at least one vacant space 33e is formed among the suspension plate 33a, the outer frame 33b and the at least one bracket 33c for allowing the gas to flow through.

In addition, the first surface 331a of the suspension plate 33a has the bulge 33f. In this embodiment, the formation of the bulge 33f may be made by using an etching process, in which the region between the periphery of the bulge 33f and the junction at the least one bracket 33c is partially removed to be concaved. Accordingly, the bulge 33f of the suspension plate 33a is higher than the first surface 331a, and a stepped structure is formed.

Figure 5A:
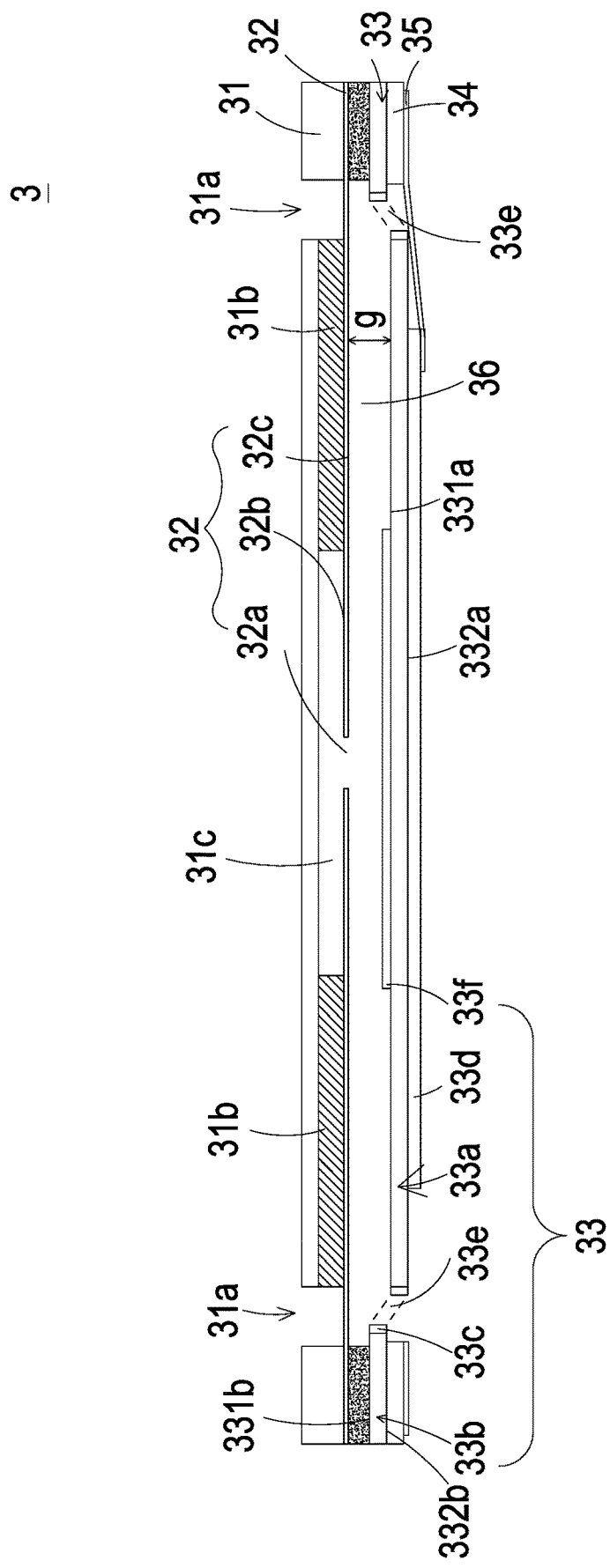
FIG. 5A is a schematic cross-sectional view illustrating the actuator of the portable gas detecting device of the present disclosure.

As shown in FIG. 5A, in this embodiment, the suspension plate 33a may be further processed by using a stamping method, by which the outer frame 33b, the bracket 33c and the suspension plate 33a have a concave profile in cross section. The concave distance can be adjusted through changing an inclined angle of the at least one bracket 33c formed between the suspension plate 33a and the outer frame 33b. Consequently, the top surface of the bulge 33f of the suspension plate 33a and the first surface 331a of the suspension plate 33a are not coplanar with the assembling surface 331b of the outer frame 33b. Namely, the top surface of the bulge 33f of the suspension plate 33a and the first surface 331a of the suspension plate 33a are lower than the assembling surface 331b of the outer frame 33b, and the second surface 332a of the suspension plate 33a is lower than the bottom surface 332b of the outer frame 33b. In the embodiment, the piezoelectric element 33d is attached on the second surface 332a of the suspension plate 33a and is disposed opposite to the bulge 33f. In response to an applied driving voltage, the piezoelectric element 33d is subjected to a deformation owing to the piezoelectric effect so as to drive the suspension plate 33a to bend and vibrate. In an embodiment, a small amount of adhesive is applied to the assembling surface 331b of the outer frame 33b, and the piezoelectric actuator 33 is attached on the fixed part 32c of the resonance plate 32 after a hot pressing process. Therefore, the piezoelectric actuator 33 and the resonance plate 32 are assembled together.

In addition, the insulation plate 34 and the conducting plate 35 are both thin frame-shaped plates, which are stacked sequentially under the piezoelectric actuator 33. In this embodiment, the insulation plate 34 is attached on the bottom surface 332b of the outer frame 33b of the piezoelectric actuator 33.

Please refer to FIG. 5A. The gas inlet plate 31, the resonance plate 32, the piezoelectric actuator 33, the insulation plate 34 and the conducting plate 35 of the actuator 3 are stacked on each other sequentially. A chamber gap g is formed between the first surface 331a of the suspension plate 33a and the resonance plate 32. Since the chamber gap g influences the transportation effect of the actuator 3, it is important to maintain the chamber gap g at a fixed depth for the actuator 3 in providing stable transportation efficiency. The suspension plate 33a of the actuator 3 is processed by the stamping method as described above to be concaved in a direction away from the resonance plate 32. Consequently, the first surface 331a of the suspension plate 33a is not coplanar with the assembling surface 331b of the outer frame 33b. Namely, the first surface 331a of the suspension plate 33a is lower than the assembling surface 331b of the outer frame 33b, and the second surface 332a of the suspension plate 33a is lower than the bottom surface 332b of the outer frame 33b. As a result, a chamber space 36 is formed between the concaved suspension plate 33a of the piezoelectric actuator 33 and the resonance plate 32, and the chamber space 36 has an adjustable interval (e.g., chamber gap g). The present disclosure provides an improved structure in which the suspension plate 33a of the piezoelectric actuator 33 is processed by the stamping method to be concaved. Therefore, the required chamber space 36 can be formed by adjusting the concaved distance of the suspension plate 33a, which simplifies the structural design regarding the adjustment of the chamber space 36, and achieves the advantages of simplifying the process and shortening the processing time.

Figure 5B:
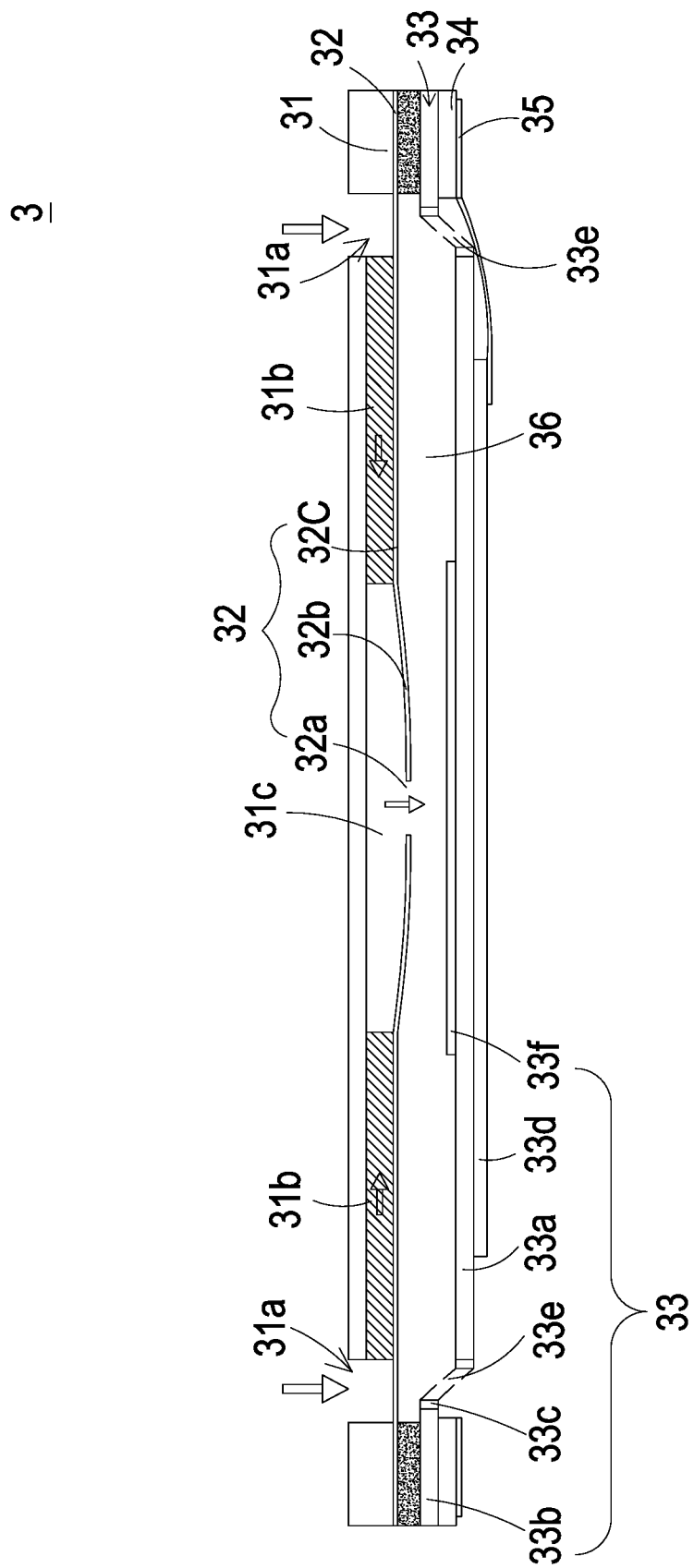
FIGS. 5B, 5C and 5D schematically illustrate the actions of the actuator of the portable gas detecting device of the present disclosure.
Figure 5C:
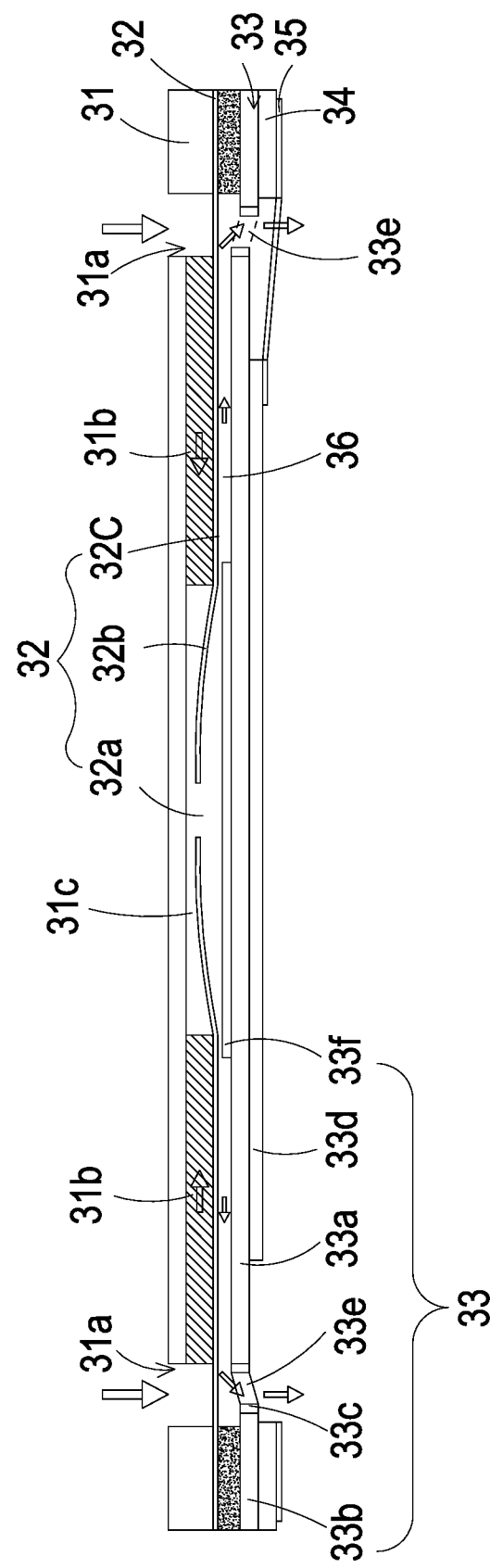
Figure 5D:
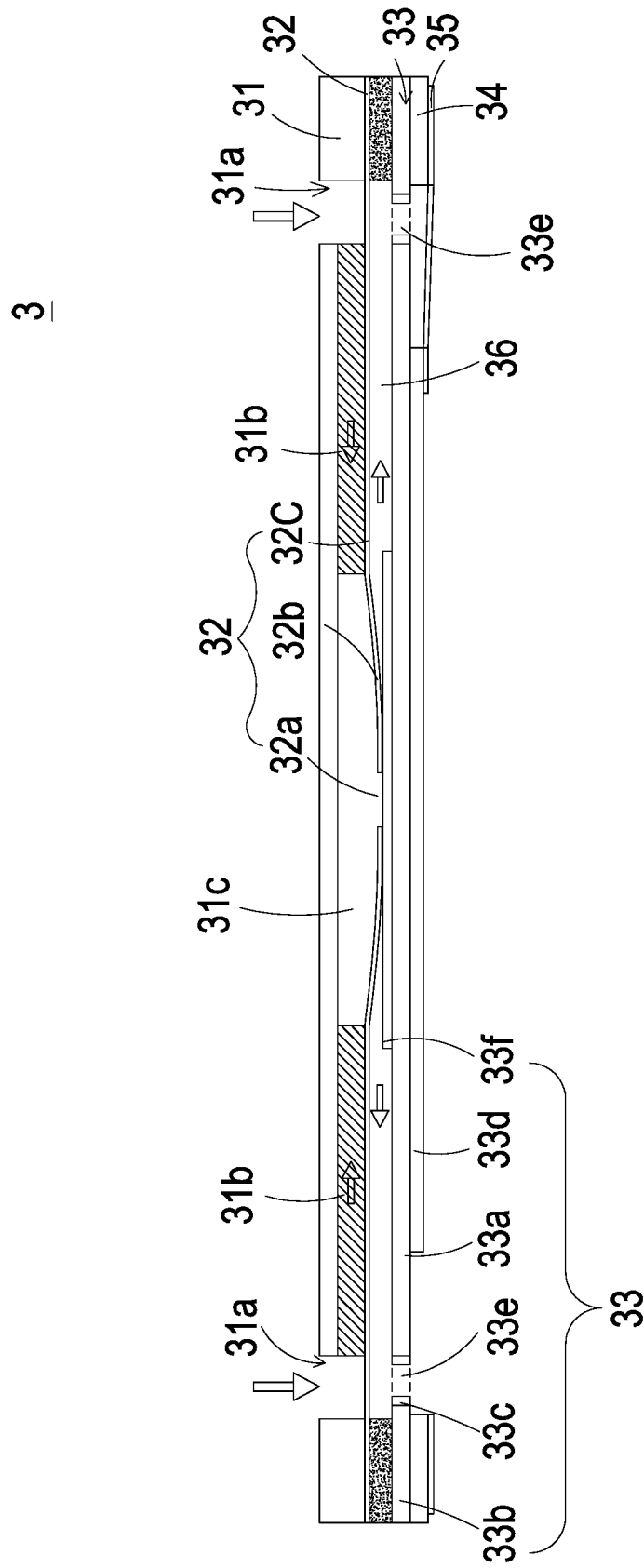

FIGS. 5B to 5D schematically illustrate the actions of the actuator 3 of FIG. 5A. Please refer to FIG. 5B. When a driving voltage is applied to the piezoelectric element 33d of the piezoelectric actuator 33, the piezoelectric element 33d deforms to drive the suspension plate 33a to move in the direction away from the gas inlet plate 31. Meanwhile, the volume of the chamber space 36 is increased, and a negative pressure is formed in the chamber space 36 so that the air in the convergence chamber 31c is inhaled into the chamber space 36. At the same time, the resonance plate 32 is in resonance with the piezoelectric actuator 33 to move in the direction away from the gas inlet plate 31, so that the volume of the convergence chamber 31c is expanded. Since the air in the convergence chamber 31c is transported to the chamber space 36, a negative pressure is formed in the convergence chamber 31c. The negative pressure allows the air to be inhaled through the convergence channel 31b and the inlet aperture 31a to the convergence chamber 31c. Please refer to FIG. 5C. The piezoelectric element 33d drives the suspension plate 33a to move toward the gas inlet plate 31, and the volume of the chamber space 36 is compressed, so that the gas in the chamber space 36 is forced to flow through the vacant space 33e in the direction away from the gas inlet plate 31. Thereby, the air transportation efficacy is achieved. Meanwhile, the resonance plate 32 is moved toward the gas inlet plate 31 in resonance with the suspension plate 33a, and the air in the convergence chamber 31c is pushed to move toward the chamber space 36 synchronously. Please refer to FIG. 5D. When the suspension plate 33a is driven to move in the direction away from the gas inlet plate 31, the resonance plate 32 is moved in the direction away from the gas inlet plate 31 in resonance with the suspension plate 33a. Meanwhile, the air in the chamber space 36 is compressed by the resonance plate 32 and is transferred toward the vacant space 33e. The volume of the convergence chamber 31c is expanded, and the air is allowed to flow through the inlet aperture 31a and the convergence channel 31b and converge in the convergence chamber 31c continuously. By repeating the above steps, the air is continuously introduced through the inlet aperture 31a into the actuator 3, and then the air is transferred through the vacant space 33e in the direction away from the gas inlet plate 31. Consequently, the efficacy of transferring the air to the gas sensor 2 is achieved.

The air is continuously provided to the gas sensor 2 for monitoring, thus the efficiency of monitoring is increased.

Please refer to FIG. 5A. In another embodiment, by utilizing the micro-electromechanical system, the actuator 3 is a micro-electromechanical system gas pump. Preferably but not exclusively, the gas inlet plate 31, the resonance plate 32, the piezoelectric actuator 33, the insulation plate 34 and the conducting plate 35 are manufactured by surface micromachining to reduce the volume of the actuator 3.

Figure 6:
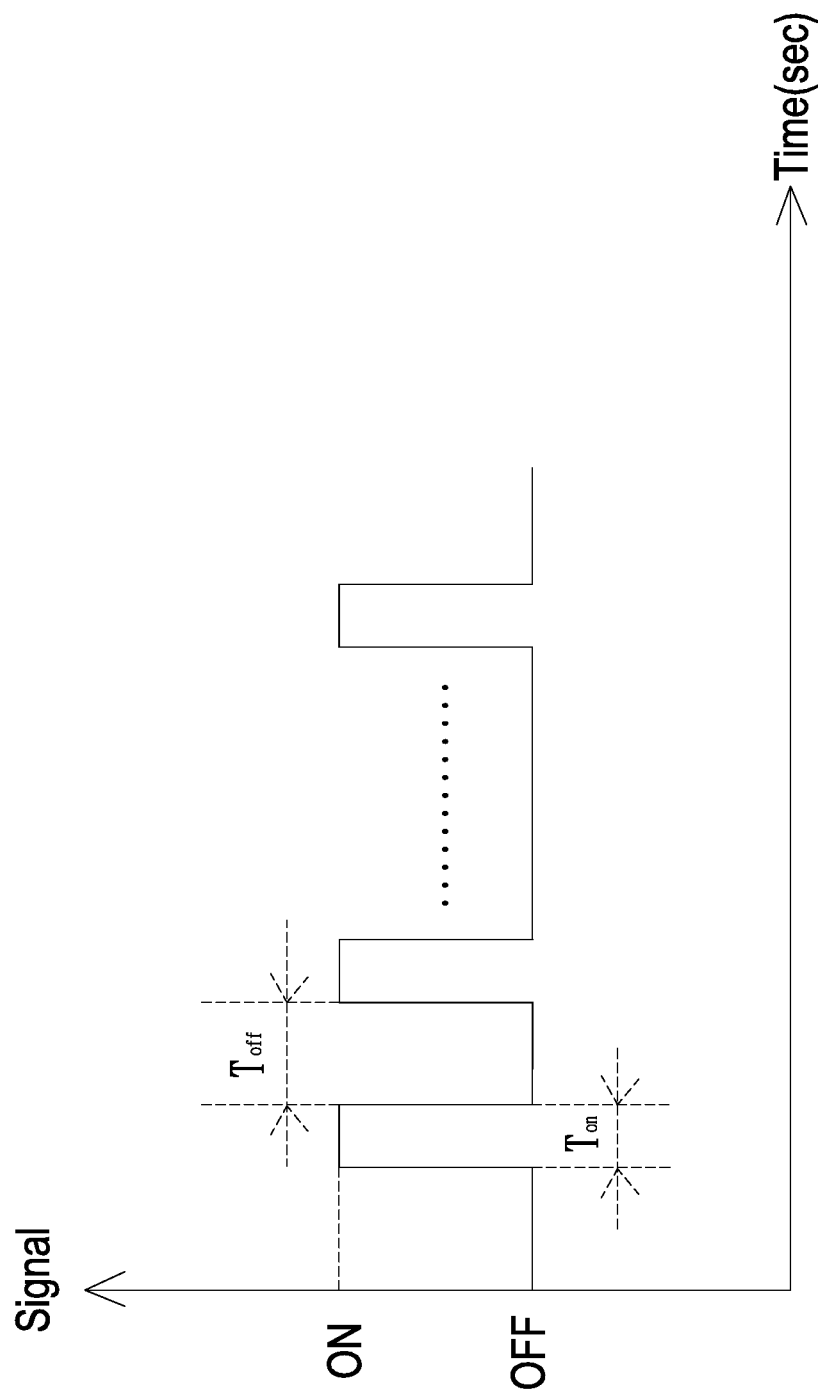
FIG. 6 schematically illustrates the actuator driven by an instantaneous sampling pulse of the portable gas detecting device of the present disclosure.

As described above, the present disclosure provides a structural design that the actuator 3 and the gas sensor 2 are disposed in a detecting chamber 1 for monitoring gas, wherein the actuator 3 and the gas sensor 2 are miniaturized to form a portable gas detecting device 100. For example, the actuator 3, the gas sensor 2 and the detecting chamber 1 are constructed in a mobile phone (as shown in FIG. 3), and thus the mobile phone becomes a portable gas detecting device 100 by which the user is capable of monitoring the environmental gas everywhere and any time. In addition, in order to provide the portable gas detecting device 100 capable of monitoring gas with accurate sensitivity and immediate response, the present disclosure utilizes the actuations of the actuator 3 to drive the flow of gas so as to improve the efficiency of monitoring. Meanwhile, the actuator 3 is driven by a pulse to initiate immediate sampling operation, controlling a trace of gas to flow into the detecting chamber 1 to form a stable airflow, so that the gas detection with accurate sensitivity and immediate response is achieved. Namely, the actuator 3 of the present disclosure is actuated immediately once it receives an actuating signal, and is stopped immediately once it does not receive the actuating signal. Therefore, the inertial driving way of the conventional fan, which requires a period of acceleration time or deceleration time while activating or deactivating the fan, is completely modified and replaced. In addition, when the actuating signal is applied to the piezoelectric actuator 33 of the actuator 3, the piezoelectric actuator 33 is actuated immediately and causes a resonance effect. The caused resonance effect introduces the gas outside the detecting chamber 1 into the detecting chamber 1 for sampling. The sampling in the detecting chamber 1 may be a continuous sampling or an intermittent sampling. In the embodiment of the present disclosure, the sampling in the detecting chamber 1 is an instantaneous and intermittent sampling. As shown in FIG. 6, the actuator 3 is driven by an instantaneous sampling pulse, and the actuator 3 is controlled to start or stop in an extremely short time by the instantaneous sampling pulse. The ratio of a start time (Ton) and a stop time (Toff) of the instantaneous sampling pulse is between 0.001 and 0.5. Preferably, the ratio of a start time (Ton) and a stop time (Toff) of the instantaneous sampling pulse is between 0.01 and 0.2. Being driven by the instantaneous sampling pulse, sampling operation in the detecting chamber 1 is performed immediately, and the gas outside the detecting chamber 1 is inhaled through the inlet 14 to the detecting chamber 1 for forming a stable airflow environment. In the stable airflow environment, the gas molecule is dissolved in or bonded to the reaction material on the surface of the gas sensor 2 for reacting. Therefore, the gas sensor 2 possesses accurate sensitivity and monitors with immediate response. The sensing sensitivity of the gas sensor 2 is prevented from being affected and distorted by high or disordered flow rate of gas.

From the above descriptions, the present disclosure provides a portable gas detecting device. The actuator of the portable gas detecting device is actuated to drive the flow of gas and improve the efficiency of monitoring. The actuator is driven by a pulse to start sampling in the detecting chamber immediately. A trace of gas is controlled to flow into the detecting chamber to form a stable airflow environment. Due to the stable airflow environment, the gas sensor possesses accurate sensitivity and monitors with immediate response. In addition, the actuator and the gas sensor are miniaturized for being portable, which allows the user to monitor the environmental gas everywhere and any time. Moreover, a partition is disposed in the detecting chamber for separating the gas sensor and the actuator from each other, so that the gas sensor and the actuator are prevented from interfering each other. Furthermore, the structure of the actuator is miniaturized, which benefits the miniaturization of the device to which the actuator is applied. Therefore, the device is portable and is allowed to monitor everywhere and any time, which is industrially valuable.

While the disclosure has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A portable gas detecting device, comprising:
   at least one detecting chamber having at least one inlet and at least one outlet;
   at least one gas sensor disposed in the detecting chamber and configured for monitoring gas inside the detecting chamber; and
   at least one actuator disposed in the detecting chamber and comprising a piezoelectric actuator generating a resonance effect when an actuating signal is applied to the piezoelectric actuator, by which the gas outside the detecting chamber is introduced into the detecting chamber for sampling, wherein the at least one actuator is driven by an instantaneous pulse to make gas flow into the detecting chamber, thereby forming a stable airflow therein, wherein in the stable airflow, a gas molecule of the gas is dissolved in or bonded to a reaction material on a surface of the gas sensor for reacting.

2. The portable gas detecting device according to claim 1, wherein a ratio of start time/stop time of the instantaneous pulse is between 0.001 and 0.5.

3. The portable gas detecting device according to claim 1, wherein a ratio of start time/stop time of the instantaneous pulse is between 0.01 and 0.2.

4. The portable gas detecting device according to claim 1, wherein an interior space inside the detecting chamber is divided into a first compartment and a second compartment by a partition, the inlet is in fluid communication with the first compartment, and the outlet is in fluid communication with the second compartment, wherein the partition has a communicating hole, the first compartment and the second compartment are in fluid communication with each other through the communicating hole, and the least one gas sensor is assembled in the first compartment.

5. The portable gas detecting device according to claim 4, wherein the actuator is fixed within the second compartment, and the actuator is separated from the at least one gas sensor.

6. The portable gas detecting device according to claim 1, wherein the at least one gas sensor comprises at least one selected from the group consisting of an oxygen sensor, a carbon monoxide sensor, a carbon dioxide sensor and combinations thereof.

7. The portable gas detecting device according to claim 1, wherein the at least one gas sensor comprises a volatile organic compound sensor.

8. The portable gas detecting device according to claim 1, wherein the actuator is a micro-electromechanical system gas pump.

9. The portable gas detecting device according to claim 1, wherein actuator is a gas pump and comprises:
   a gas inlet plate having at least one inlet aperture, at least one convergence channel and a convergence chamber, wherein the at least one inlet aperture allows the air to flow in, the at least one convergence channel is disposed corresponding to the at least one inlet aperture and guides the air from the at least one inlet aperture toward the convergence chamber;
   a resonance plate having a central aperture and a movable part, wherein the central aperture is aligned with the convergence chamber, and the movable part surrounds the central aperture; and
   a piezoelectric actuator aligned with the resonance plate, wherein a gap is formed between the resonance plate and the piezoelectric actuator to define a chamber space, so that the air from the at least one inlet aperture of the gas inlet plate is converged to the convergence chamber along the at least one convergence channel and flows through the central aperture of the resonance plate when the piezoelectric actuator is enabled, whereby the air is further transferred through a resonance between the piezoelectric actuator and the movable part of the resonance plate.

10. The portable gas detecting device according to claim 9, wherein the piezoelectric actuator comprises:
   a suspension plate having a first surface, a second surface and a bulge, wherein the bulge is formed on the first surface;
   an outer frame arranged around the suspension plate and having an assembling surface;
   at least one bracket connected between the suspension plate and the outer frame for elastically supporting the suspension plate; and
   a piezoelectric element attached on the second surface of the suspension plate, wherein when a voltage is applied to the piezoelectric element, the suspension plate is driven to undergo a bending vibration,
   wherein the at least one bracket is formed between the suspension plate and the outer frame, the first surface of the suspension plate and the assembling surface of the outer frame are non-coplanar, and the chamber space is maintained between the first surface of the suspension plate and the resonance plate.

11. The portable gas detecting device according to claim 9, wherein the gas pump further comprises a conducting plate and an insulation plate, wherein the gas inlet plate, the resonance plate, the piezoelectric actuator, the insulation plate and the conducting plate are stacked sequentially.

* * * * *